United States Patent [19]

Guirguis

[11] Patent Number: 5,139,031
[45] Date of Patent: Aug. 18, 1992

[54] METHOD AND DEVICE FOR CYTOLOGY AND MICROBIOLOGICAL TESTING

[75] Inventor: Raouf A. Guirguis, Rockville, Md.

[73] Assignee: La Mina Ltd., British Virgin Isls.

[21] Appl. No.: 680,896

[22] Filed: Apr. 8, 1991

Related U.S. Application Data

[63] Continuation-in-part of Ser. No. 553,585, Jul. 18, 1990, Pat. No. 5,042,502, which is a continuation-in-part of Ser. No. 408,547, Sep. 18, 1989, Pat. No. 5,024,238, which is a continuation-in-part of Ser. No. 411,041, Sep. 22, 1989, Pat. No. 5,953,561.

[51] Int. Cl.$^5$ .............................................. A61B 5/00
[52] U.S. Cl. ............................... 128/771; 604/406
[58] Field of Search ....................... 128/760, 762, 771; 604/318, 404, 406; 422/56, 60

[56] References Cited

U.S. PATENT DOCUMENTS

| | | | |
|---|---|---|---|
| 3,722,502 | 3/1973 | Besuner et al. | 128/771 |
| 4,170,056 | 10/1979 | Meyst et al. | 604/406 |
| 4,473,530 | 9/1984 | Villa-Real | 128/771 |
| 4,685,472 | 8/1987 | Muto | 128/760 |

Primary Examiner—Max Hindenburg
Attorney, Agent, or Firm—John S. Hale

[57] ABSTRACT

The present invention is directed towards an apparatus and a method which can use immunoassay in sample treatment apparatus for diagnostic and testing purposes of dialysis fluid or urine by concentrating the urinary sediments on a first membrane and concentrating bacteria on a second membrane. Urine is transported through the tubular container under pressure to flow through the sample container which separately screens off the urinary sediments and the bacteria for collection and testing.

33 Claims, 5 Drawing Sheets

METHOD AND DEVICE FOR CYTOLOGY AND MICROBIOLOGICAL TESTING

RELATED CASES

This application is a is a continuation-in-part application of U.S. patent application Ser. No. 07/553,585 filed Jul. 18, 1990, U.S. Pat. No. 5,042,502 which is a continuation-in-part application of U.S. patent applications Ser. No. 07/408,547 filed Sep. 18, 1989 U.S. Pat. No. 5,024,238 and Ser. No. 07/411,041 filed Sep. 22, 1989, U.S. Pat. No. 4,953,561.

BACKGROUND OF THE INVENTION

The present invention is directed to medical and laboratory biological specimen collecting and testing apparatus. Diagnostic cytology is the area of clinical pathology in which diagnoses are made based on microscopic examination of cell and other biological samples taken from many body sites. The accuracy of the diagnosis depends on both adequate patient sampling and culture and slide preparation procedures that result in optimally interpretable specimens.

In peritoneal dialysis patients, it is important not only to culture the fluid from the chronic ambulatory patients, but also to determine whether or not there are inflammatory cells present in that fluid. Patients who have frank peritonitis with rebound tenderness, guarding, fever and leukocytosis are not difficult to diagnose. Nephrologists seek early diagnoses of those patients who have some symptomology, but have mild tenderness, low grade fever and no abdominal rigidity.

Nephrologists will frequently culture the dialysate in one of many ways, demonstrating the fact that there is no perfect method to detect early peritonitis. Most nephrologists will also extract some fluid from the abdominal cavity and do a cell count on a hemocytometer. The latter is to support the results of the culture, which in and of itself may not distinguish between true peritonitis and a simple colonization of bacteria.

The organisms which are most common in peritonitis are the enterobacteriacae, particularly *E. coli* and the coagulase negative staphylcoccus. The latter is particularly a problem since it is a commensal organism frequently found as a contaminant. Therefore, when one examines a minimum of fifty mililiters of fluid and finds white cells and bacteria, the evidence becomes stronger that an early inflammatory disease is present and therapy can be started with a much better clinical outcome and at much less cost.

Under normal conditions, urine contains a small number of cells and other particulate matter shed from the entire length of the urinary tract. These materials are usually known as urinary sediments. Typical urinary sediments consist of red blood cells, white blood cells, epithelial cells, casts, mucus and crystals. In addition, sporatic urinary sediment such as bacteria, yeast, parasites and spermatozoa occur in patients suffering from various types of disorders or engaging in particular activities. With disease, these cells as well as other formed elements are often increased and may help to localize the site and type of injury. For example, excessive numbers of red blood cells may indicate tumor, stones or imflammation. Excessive number of leukocytes may indicate infection or other inflammatory disease. In contrast to the hypocellular nature of normal urine, neoplastic cells (e.g., transitional, squamous and columnar cells) are shed more frequently in malignant conditions of the bladder epithelium.

Until recently the technique of preparing the best possible specimen has not drawn as much attention as it deserves. Preparative shortcomings such as uneven cell distribution and variable staining results that result in suboptimal slides can marginally be tolerated because the human observer can still evaluate these slides and correct for inconsistencies. Recently, however, interest in a better quality slide has increased. The increased use of fine-needle aspirates for diagnostic purposes, greater use of image cytometry and a greater concern about cytology quality control issues are a few of the reasons behind the movement to improve preparation techniques. Additional tests performed with new technologies such as immunocytochemistry and image analysis are being evaluated. These tests require high quality specimens to fully achieve their capabilities. Clearly, preparation and fixation protocols that are the same and reproducible for each sample type are needed.

Membrane filter techniques are an improvement because they are performed in the cytology laboratory where they can be better controlled. An advantage of using a cell suspension is that the sample can be dispersed to minimize large clumps and provide a more even cell distribution in the resulting slide. Typically, the cell suspension is dispersed by vortexing or with a syringe.

In the membrane filtration technique the cell suspension is both concentrated and collected on a membrane filter made of cellulose or polycarbonate. This technique is used in many cases when the cell concentration is low, as in cerebrospinal fluid. Cells in body fluid or in a preservation fluid are put in a funnel, collected, rinsed and prefixed on the filter and the filter with the prefixed cells is then put on a slide. Because the filter background interferes with the inspection of the cells, procedures have been developed to dissolve the filter. However, because the procedure for dissolving the filter also affects the morphology of the cells, this technique does carry some risks.

Although urine and dialysis fluid are the specimens discussed for diagnosis, other fluids such as seminal, synovial, pleural, pericardial, peritoneal, amniotic and sweat fluids are associated with specific conditions and diseases. It is important during the collection handling of biological fluid specimens that the potential of specimen deterioration, contamination and the spread of any infection from the specimen be minimized.

A typical specimen collecting apparatus is shown by U.S. Pat. No. 4,741,S46. This apparatus includes a base stand which supports the specimen vial in an upright position. A funnel is inserted in the open end of the specimen vial and surrounds and encloses the upper portion of the vial. The base stand has an upwardly extending tubular wall which at least partially surrounds the vial in connection with the cap and allows the user to remove the vial without touching the surface or coming in contact with the specimen. Examples of various types of liquid containers for collecting and transporting urine are shown by U.S. Pat. Nos. 3,777,739; 3,881,465; 4,042,337; 4,084,937; 4,244,920; 4,492,258 and 4,700,714.

Another specimen collection device shown by U.S. Pat. No. 4,040,791 discloses a collection receptacle having a nipple upon which is mounted a specimen container which receives a predetermined amount of the specimen in a sealed condition. The specimen container is provided with an integrally formed cap which is placed over the opening in which the collector nipple is inserted. U.S. Pat. No. 4,557,274 discloses a midstream urine collector having a funnel which transmits urine into a cup member which is covered by a membrane cover.

A combined strip testing device and collection apparatus is shown by U.S. Pat. No. 4,473,530 and is directed to an apparatus which integrates testing and collection by having chemical reagent test strips present within the tube together with specific gravity reading means allowing immediate testing of the urine. U.S. Pat. No. 4,573,983 is directed towards a liquid collection system having an antiseptic member on the discharge section which uses a filter of air and bacteria impervious material to filter the urine.

A number of investigators involved in automated measurement of cervical smears have developed instruments that incorporated cell collection techniques. One group developed an instrument that includes a rotor device to disperse cells aggregated by mucus or other non-cellular bonds. Use of the rotor results in a high degree of cell dispersion and a reduction of cell clumps while maintaining diagnostic abnormal cell clusters. Then the desired number of cells are collected on a polycarbonate filter membrane and deposited on a slide by simultaneous pressure and fixation. The filtration removes much of the non-diagnostic background debris and most red blood cells resulting in a cleaner slide without losing important diagnostic clues.

Cytic Corp. has enhanced and refined this earlier instrumentation in designing the ThinPrep Processor. Gentle dispersion breaks up large clumps while keeping diagnostic clusters intact. Most red blood cells and insignificant debris are removed. The cellular material is then transferred to the slide with controlled density. This process is non-aerosoling, non-contaminating, low cost and fully automated.

It is therefore desirable to provide an easy to handle disposable apparatus and a method which transports a fluid sample through staged filters to capture a concentrated amount of cell particulate matter and bacteria from the fluid for testing.

BRIEF SUMMARY OF THE INVENTION

The invention is directed toward a removable easily separated shuttle system offers a relatively simple method for removal of the cellular components, sediments and bacteriological components of the fluid sample. In the device, staged filtration is essential to remove different particulate matter in the fluid sample for use with difficult tests. The inventive device is in the form of a plurality of stackable two-piece specimen containers each of which has a filter membrane with a different size porosity. A male member of the two-piece container is threaded into a female member with the housings of both members being provided with throughgoing bores allowing fluid flow therethrough. The urine or dialysis fluid is pulled from a sample container by a syringe through stacked containers where it engages and passes through a first filter membrane having a 5 micron filter particle size, which screens cells and cell debris onto the membrane while allowing passage of filtered fluid into a second container housing a filter membrane having a 4.5 micron filter particle size which screens bacteria and causes the same to be concentrated on the surface of the membrane.

It is thus an object of the invention to collect and concentrate specific bacteria from the fluid for future deposit into a culture medium and to collect cells and other particulate matter in a separate compartment for placement on a slide. Previously such testing has been accomplished by a series of differing tests involving a number of different containers and expensive laboratory equipment of a limited sensitivity.

In the accompanying drawings, there is shown an illustrative embodiment of the invention from which these and other of objectives, novel features and advantages will be readily apparent.

DETAILED DESCRIPTION OF THE INVENTION

The preferred embodiment and best mode of the invention is seen in FIGS. 1 through 4. The initial collection of the sample fluid is normally housed in a graduated 100 ml container 10 as shown in phantom in FIGS. 1 and 2. Such a container is currently manufactured by Becton Dickinson Labware under the 8-168-designation 4013 specimen container. This collection container holds 4.5 oz. (approx. 133 ml) of fluid and is graduated with a polyethylene snap lid.

Figure 1:
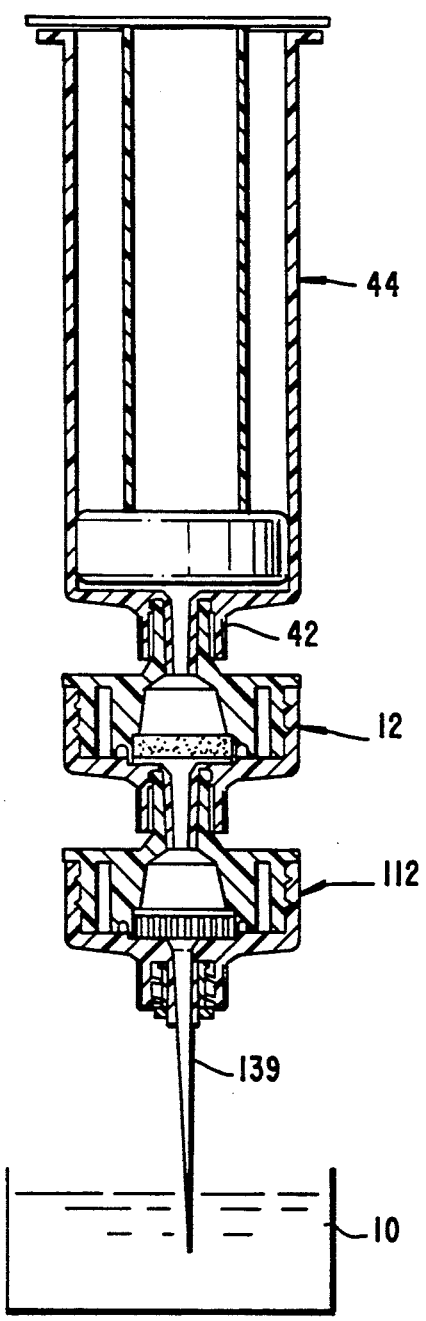
FIG. 1 is a cross sectional schematic view of the inventive staged shuttle cytology prior to displacement of the fluid sample through the shuttle container.
Figure 2:
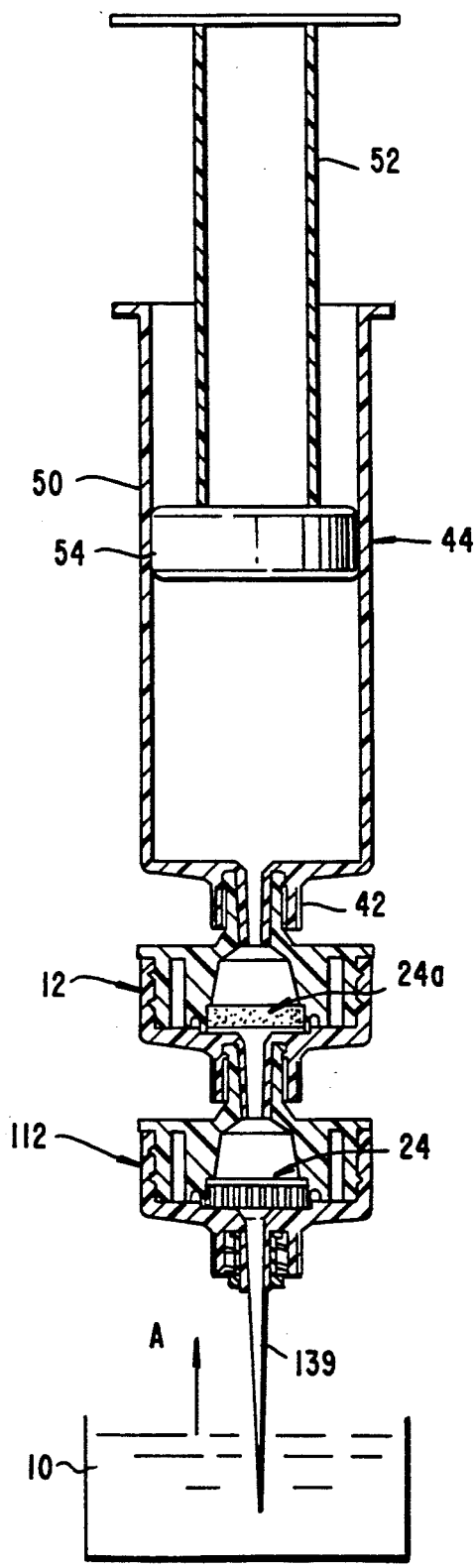
FIG. 2 is a cross sectional schematic view of the inventive staged shuttle cytology apparatus mounted on a syringe showing the stacked shuttle containers as the fluid to be tested passes through the filter containers entering the syringe with direction of movement shown by arrow A.
Figure 3:
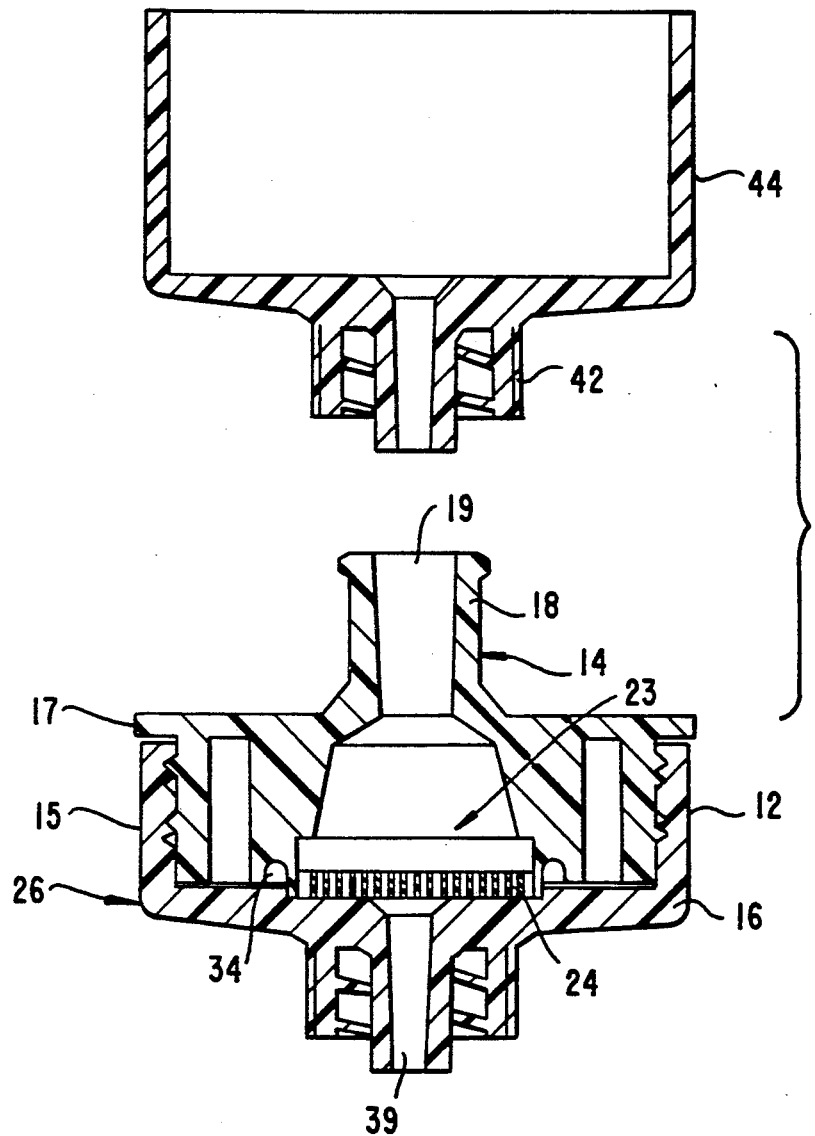
FIG. 3 is an enlarged cross sectional view of a shuttle container of the shuttle apparatus shown in FIG. 1 in relation to an exploded cross sectional view of the syringe barrel.

A stacked shuttle container assembly 12 as more clearly shown in FIGS. 1 and 2 is provided with a plurality of stacked shuttle containers. Each container is easily opened and is constructed with a simple two-piece construction comprising a male filter membrane carrying member 14 and a female connector member 26 screwed onto the male member. The shuttle container assembly 12 is mounted onto a luer lock 42 of a syringe 44 as will be more fully described. The male filter membrane member 14 is provided with an outer cylindrical wall 15 having a threaded external surface 21, a base 16 which extends past the cylindrical wall 15 to form a lip 17, and a male nipple 18 which extends outward from the base in an opposite direction from wall 15. The nipple 18 is provided with an end flange which is adapted to be threaded into the threaded luer lock 42 of the syringe 44 and defines a throughgoing bore 19 which leads into chamber 20 defined by an inner inclined wall 22 of the male member. The inner wall 22 has a cylindrical exterior surface and is spaced from the inner surface of outer wall 22 to define a channel 27. An annular step or membrane seat 23 is cut into the inner surface of wall 22 to hold membrane 24. An annular channel 25 is cut into the surface of stepped end 28 of the inner wall 22 allowing the stepped end to fit over locking prongs 34 extending from the female member thus holding the male and female members in a sealed relationship while providing a safety stop for the membrane 24.

Figure 5:
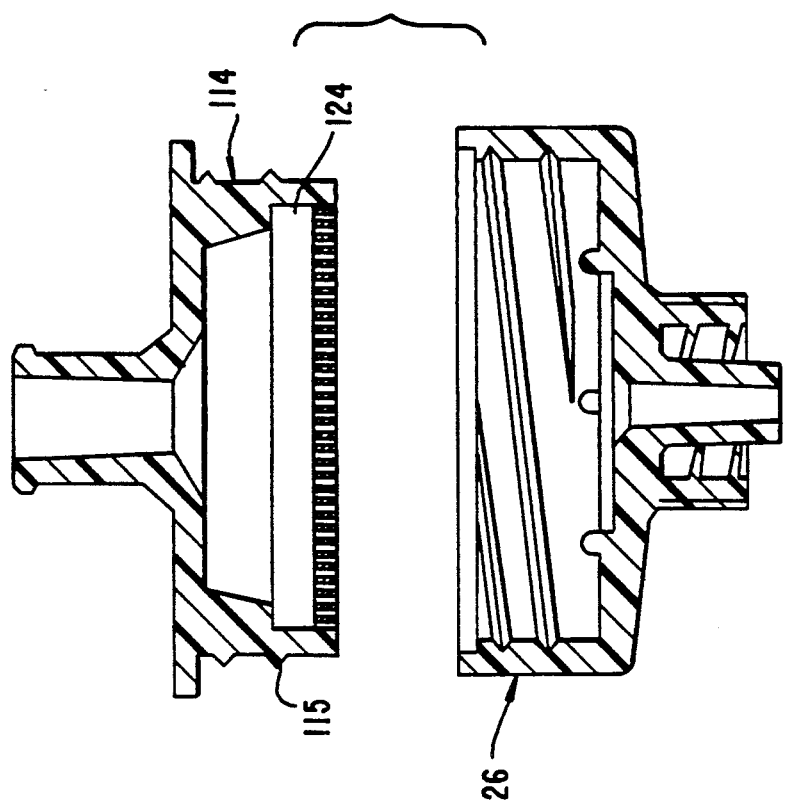
FIG. 5 is an alternate sized exploded cross sectional view of another shuttle container showing a male membrane member and female connector member.
Figure 4:
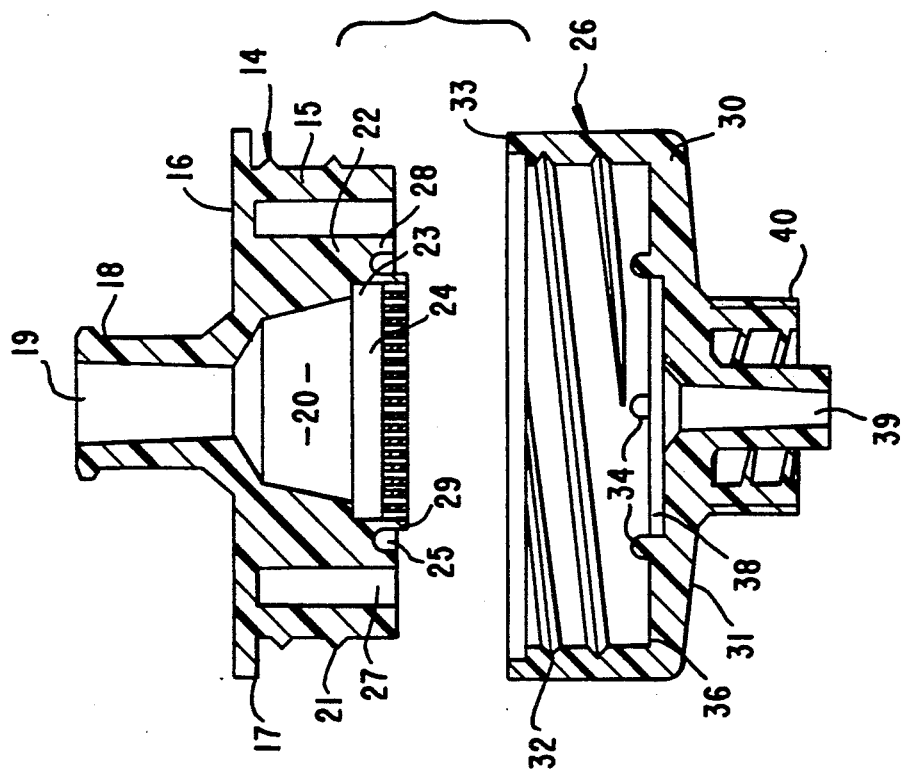
FIG. 4 is an exploded cross sectional view of the shuttle container shown in FIG. 3 showing the male membrane member and female connector member.

The female connector member 26 as shown in FIGS. 4 and 5 has an outer cylindrical housing 30 with a base 31. The housing is threaded on its inner surface 32 for engagement with the threaded external surface 21 of wall 15. The planar end wall 33 of housing 30 abuts against the outwardly extending flange or lip 17 when the male and female members are screwed together. The base inner surface, which in combination with the inner wall surface of housing 30 defines the interior configuration of the female member, is concentrically stepped so that the outer step 36 abuts against the end of walls 15 and 22 and an inner step 38 abuts against membrane 24 and the distal stepped portion 29 of stepped end 28. The base 31 is provided with a threaded luer lock 40 on its exterior surface and defines a throughgoing bore 39 with a frustro conical end which leads to membrane 24 and chamber 20. As previously noted, nipple 18 of the shuttle container is fitted with a threaded projection which is adapted to fit onto the luer lock 42 of a 30 cc syringe 44, manufactured by Becton Dickinson & Co. on the luer lock 40 of a companion shuttle container 12. It should be noted that any pump type device could be used in place of the syringe 44 as for example an autovial spunglass filter manufactured by Genex Corporation. The syringe 44 has a barrel 50 with associated luer lock 42, piston 52 and piston head 54. While the invention can be used for any body fluid it is primarily designed for use with concentrated dialysis fluid and urine and for collecting associated sediments and/or bacteria for use in testing for various kinds of disease.

As shown in FIGS. 1 through 7 the shuttle container assembly 12 is constructed of polystyrene. The male member 14 of shuttle container assembly 12 as shown in FIG. 4 contains a nitrocellulose membrane filter 24a with a filter size of 13 mm diameter and a porosity of approximately 0.45 microns.

A second identical shuttle container 112 is removably mounted to shuttle container 12 by threading nipple 18 onto the luer lock 40. A needle 139 is mounted in bore 39 of shuttle 112 so that its flared end seats in the flared frustro conical end portion of bore 39. This second shuttle is provided with a polycarbonate membrane filter 24 with a filter size of 13 mm diameter and a porosity of 5 microns.

An alternative shuttle container is shown in FIG. 5 which can be substituted for shuttle container 112. This shuttle container differs from the previously described shuttle container in that the male member 114 is designed to hold a 25 mm diameter polycarbonate membrane 124 of 0.45 microns porosity and because of the greater membrane diameter size, the inner wall interior configuration 22 of male member 14 has been removed to form a single wall housing 115 which is exteriorly threaded in the same manner as male member 14.

In operation, the invention uses two membrane filters in series, each membrane being held in a separate container. The first filter from a fluid flow engagement or flow contact is a polycarbonate filter 24, which has a five-micron pore size to trap the polymorphnuclear leukocytes or even lymphocytes which are seven and one half microns in size. As the fluid transgresses through the polynuclear filter, it will then come into contact with the nitrocellulose filter 24a, containing a 0.45 micron pore size, which will trap bacteria.

Figure 7:
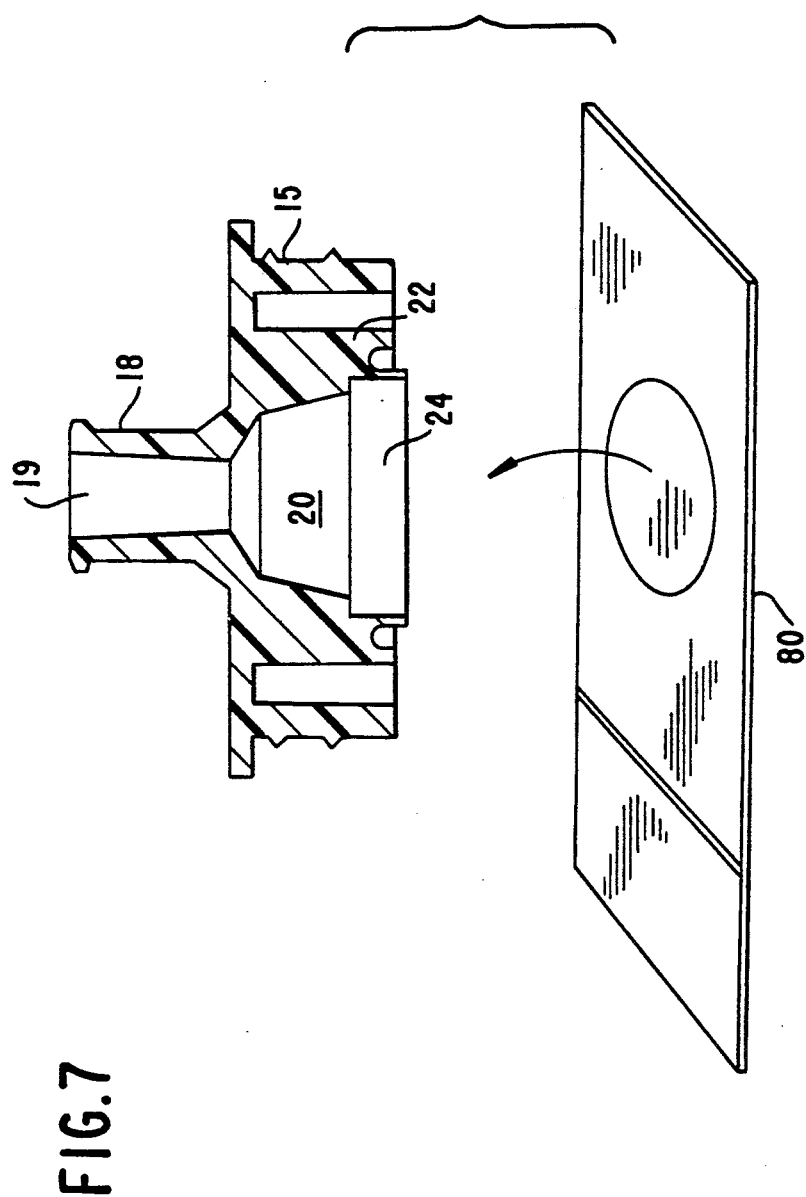
FIG. 7 is a cross sectional view of the male membrane member unscrewed from the female connector member of the removed stacked cell shuttle container being placed on a slide for cytology collection and examination.

It should be noted that various composition filters can be used and interchanged. One membrane filter that can be used for the initial fluid screening is LEUCOSORB, a leucocyte retention medium manufactured by Pall BioSupport Division of Pall Corporation. Other membranes manufactured and sold by the Pall Corporation are BIODYNE A, an unmodified nylon with surface chemistry 50% amine and 50% carboxyl group with an isoelectric point of pH 6.5; BIODYNE B, a surface-modified nylon with surface chemistry characterized by a high density of strong cationic quarternary groups (the zeta potential is positive to pH>10); BIODYNE C, a surface-modified nylon with surface chemistry characterized by a high density of anionic carboxyl groups (the zeta potential is negative to pH>3; and LO-PRODYNE, a low protein binding nylon 66 membrane with a tightly controlled microporous structure with high voids volume for rapid, efficient throughput of liquids and absolute retention of microparticles designed for cell separation and bacterial cell immunoassays. Fifty milliliters of dialysate will be pulled from container 10 through both filter membranes 24 and 24a into a syringe. After the requisite amount of dialysate has been passed through the filter membranes, the downstream container 112 and filter membrane 24 is removed. The polycarbonate membrane 24 is placed on a glass slide 80 as shown in FIG. 7 and stained with a modified Wrights stain for cytologic determination.

Thus, the method of transferring cells to a slide is that of membrane filtration (filtration of fluid specimens through membrane filters to increase cell recovery). This particular technique provides the critical feature that the cells are evenly deposited over the slide with minimal overlap as this will allow clear observation and optimal diagnostic accuracy.

It should be noted that the process of transferring or collecting cells onto a slide or membrane is largely affected by preserving or fixing the cytology specimen in the body fluid, secretions or smears.

Currently, body fluid samples are collected for cytological examinations using special containers. These containers usually contain a preservative solution for preserving the cytology specimen during shipment from the collection site to the cytology laboratory. Furthermore, cytology specimens collected from the body cavities using a swab, smear, flush or brush are also preserved in special containers with fixatives prior to transferring cells onto the slide or membrane for staining or examination.

It has been found by the present inventor that the recovery (yield) as well as the quality of the cytology preparations from fresh body fluid specimens is superior when compared to routine cytology preparations that were prepared when the same samples were preserved. This is probably due to the fact that fresh cells stick better to glass and/or membranes than those preserved in alcohol or other preservatives.

The shuttle method also allows for isolation and collection of fresh cells and/or microorganisms from the body fluids to perform DNA probing and chromosomal analysis once the cells are hemolysed by the proper buffer.

The most widely used stain for visualization of cellular changes in cytology is the Papanicolaou staining procedure. This stain, which is used for both gynecologic and non-gynecologic applications, is basically composed of blue nuclear and orange, red and green cytoplasmic counterstains. The nuclear stain demonstrates the chromatin patterns associated with normal and abnormal cells, while the cytoplasmic stains help to indicate cell origin. The success of this procedure can be attributed to the ability to observe a number of factors, including definition of nuclear detail and cell differentiation. This staining procedure also results in a multicolor preparation that is very pleasing to the eye, possibly reducing eye strain.

Since cellular detail is dependent on fixation, it is extremely important that cells be fixed immediately after being deposited on the slide. Too long a delay between preparation and fixation exposes the cells to air drying, which is detrimental to the cellular structure. Moreover, air drying artifact can adversely affect the subsequent staining results. (An exception is when the cells are stained with Wright-Giemsa, where air drying is used as the fixation step.)

New methodologies such as immunocytochemistry and image analysis require preparations that are reproducible, fast, biohazard-free and inexpensive. Different cell preparation techniques of the present invention address the issues of non-uniform cell densities, uneven cell distribution and air drying artifact. These preparations have resulted in an even distribution of cells that have superior morphology, which has improved light microscopic visualization and has allowed for the use of image cytometry instruments.

The effectiveness of transferring the cells from the filter to the slide has proved to be very high without differential cell loss. (Microscopic examination showed that the cell distribution was the same on the slide as on the filter.)

This procedure has many advantages for conventional cytology. The cells are in a predetermined area allowing for significant timesaving when screening the slide. Such problems as cells lying outside the coverslip or on the frosted end are eliminated. Because cells are lying in a single layer, they are almost always in a one focal plane when using a 10X objective—the objective most often used for the lower power screening of a slide. Even with a 40X objective, most cells are in focus. This eliminates frequent refocusing and saves time.

The minimal cell overlap achieved in this process ensures that all cells and cell groups can easily be examined with little chance for diagnostic cells to be obscured by clumps of overlapping cells or debris. Moreover, because the process takes place in the cytology laboratory, slide preparation and fixation are controlled by laboratory personnel and quality assurance is easily implemented.

Multiple specimens can be made from a single patient sample. Additional slides for other stain applications can be easily prepared. Human papilloma virus testing, for example, by newer methods such as immunocytochemistry or in-situ hybridization can be performed on the additional slides. As oncogene products or other immunocytochemical tests are developed, more slides may be necessary. The different fixations that these tests may need can easily be incorporated into the procedure since the preparation does not require the slides to be fixed in only one way.

This same slide preparation procedure can be used for virtually all forms of cytology. Furthermore, the use of completely contained disposable components addresses biohazard concerns. Ultimately, the enhanced presentation of cells, yielding improved cytologic interpretation, may expand the role of cytology by providing more consistent and reliable patient diagnosis.

Figure 6:
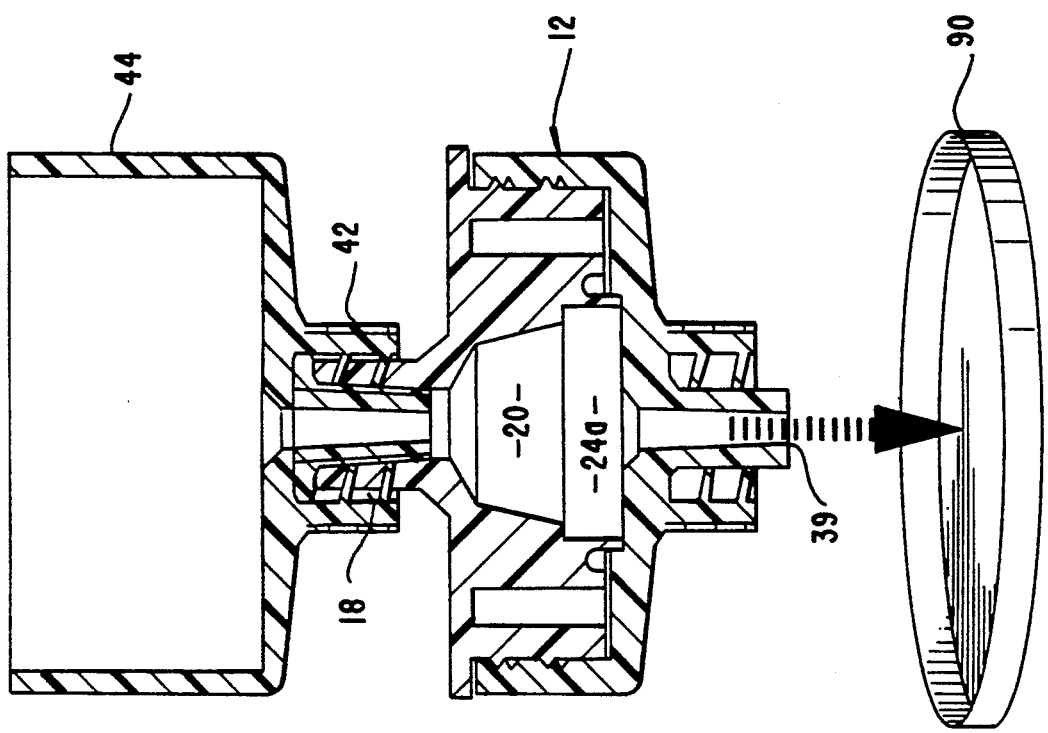
FIG. 6 is an enlarged cross sectional view of the bacteria shuttle container shown in FIG. 1 with the stacked cell shuttle container removed eluting a bacteriological sample in a microbiological culture tray.
Figure 6:
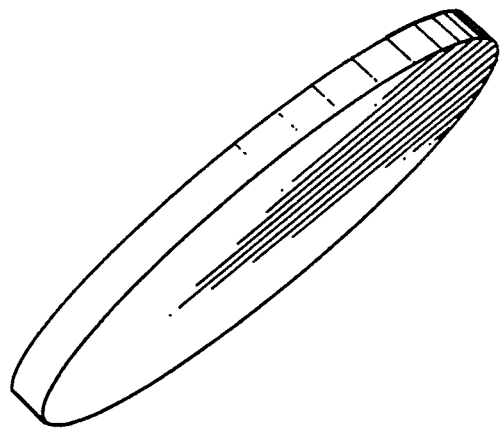

The upper filter 24a of container 12 while shown in FIG. 6 to be cultured in a standard petri dish 90 is preferably used for culturing with a Qualture device not shown but readily obtainable to determine the presence of specific bacteria colonies. The Qualture device is a plastic capsule containing a filter membrane and four nutrient pads of dehydrated, selective media. The Qualture technique uses filtration to trap microorganisms, eliminate inhibitors, and uses selective media which is dehydrated onto pads supporting the filter. The fluid sample is pipetted or placed into the Qualture capsule in amounts as small as three mls and incubated. The urine, dialysis fluid or other fluid to be cultured passes through a filter membrane in the capsule and hydrates four quadrants of dehydrated media (nutrient pads, Sartorius, W. Germany). Tergitol TTC, is useful in selecting coliforms. MFC media inhibits growth of gram positives with coliforms taking on a blue colony appearance frequently with a blue halo. Chapman media is selective for Staphylococcus inhibiting gram negative organisms. Cetrimide, the fourth quadrant is a differential media for Ps Spp producing green colonies. It does not inhibit growth of coliforms or gram negative bacteria.

The Qualture capsule was incubated at 35°-37° C. and morphology of the colonies were recorded from each of the quadrants showing growth. The Qualture technique was able to record as few as 100 colonies and isolate a variety of organisms with detection as early as 4 hours. Development of peak colony counts were at 8-12 hours using dilutions from 1,000 to 100,000 CFU/ml. Uropathogens could be presumptively diagnosed on the selective and differential media and dehydrated media was successful in supporting growth of the challenge organisms without changing colony morphology. Thus the physician or nursing station could be alerted on the same day without losing time waiting for the petri dish to be read. E. coli, Staphylococcus, S. aureus, and yeast were easily recognized by the growth pattern on the four media. Support for the presumptive diagnosis of the above are available by the indole test for E. coli, a slide latex agglutination test for S. aureus and a simple wet mount slide for yeasts. Pseudomonas known for its temperamental nature grew well, with Pa aeruginosa and Ps stutzeri being distinguishable from one another and clearly differentiated from the coliforms. A simple oxidase test supports the diagnosis of most Pseudomonas sp. E. faecalis is one of the most easily distinguishable of the pathogens because of its brick red orange color on a yellow background and no growth on MFC. The Qualture technique is more sensitive than the agar plate method and more rapid in determining a presumptive diagnosis. The device screens, isolates and presumptively diagnoses bacterial isolates in one step most often in 4-6 hours. Tests have demonstrated that recovery from fifty milliliters of fluid is excellent and sensitive.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. An apparatus for collecting cellular components and biological specimens from a fresh unpreserved body fluid for cytology and pathogen testing comprising a syringe, a plurality of specimen collection containers stacked together in fluid communication with said syringe, each specimen collection container comprising a two-piece housing comprising a male member and a female member removably mounted together, a membrane filter means is mounted in said male member adjacent a housing chamber defined by said male member, said membrane filter means allowing biological fluid flow therethrough while concentrating biological components on said membrane filter means, said membrane filter means being easily accessible for removal of the biological components collected thereon.

2. An apparatus for testing as claimed in claim 1 wherein each membrane filter means in each specimen collection container has a larger porosity than the membrane filter means in the next downstream specimen collection container.

3. An apparatus for testing as claimed in claim 1 wherein said first specimen collection container has a luer lock on one of its two-piece housing members and a nipple means adapted to be mounted into a luer lock on the other of its two-piece housing members.

4. An apparatus for testing as claimed in claim 1 wherein said male member comprises a base, a cylindrical wall extending outward from said base, an interior wall means extending outward from said base positioned inside said cylindrical wall, said interior wall means defining a membrane filter seat and a chamber adjacent said filter seat, a nipple means with a throughgoing bore extends outward from said base in the opposite direction from said cylindrical wall and said interior wall means with the throughgoing bore communicating with said interior wall means chamber.

5. An apparatus for testing as claimed in claim 4 wherein said interior wall means has a stepped end wall.

6. An apparatus for testing as claimed in claim 5 wherein said interior wall means stepped end wall defines an annular groove.

7. An apparatus for testing as claimed in claim 4 wherein said cylindrical wall has a threaded outer surface.

8. An apparatus for testing as claimed in claim 4 wherein said cylindrical wall engages said base to form a lip.

9. An apparatus for testing as claimed in claim 1 wherein said female member comprises a base means, a cylindrical wall extending outward from said base means, said base means defining a membrane filter seat and with the cylindrical wall defining a chamber adjacent said filter seat, a luer lock means with a throughgoing bore extends outward from said base means in the opposite direction from said cylindrical wall with said throughgoing bore communicating with said chamber.

10. An apparatus for testing as claimed in claim 9 wherein said cylindrical wall has a threaded inner surface.

11. An apparatus for testing as claimed in claim 9 wherein said base means is provided with prong means extending into said chamber for seating in an annular groove in the end wall of the inner wall means of the male member.

12. An apparatus for testing as claimed in claim 1 wherein said body fluid is preserved.

13. An apparatus for collecting bacteria and urinary sediments from a human fluid sample comprising a pump means, a plurality of specimen collection containers removably mounted to each other while allowing fluid passage therethrough, one of said specimen collection containers being mounted to said pump means, each of said specimen collection containers comprising a housing provided with connector means allowing the housing to be connected to other specimen collection containers, said housing comprising two mateable sections, one of said housing sections defining a chamber, a filter membrane seat defined in said one housing section positioned adjacent said chamber and a filter membrane mounted in said membrane seat, the other housing section being removably mounted to the first housing section so that said housing sections can be opened for access to the filter membrane, said other housing section including filter membrane positioning means which keeps said filter membrane in position on said filter membrane seat and defining a throughgoing bore which is adapted to hold and seat a needle, each filter membrane which is downstream of the previous filter membrane having a smaller pore size then the prior upstream filter membrane with at least one of said filter membranes retaining cellular sediments from said human fluid sample and at least one of said filter membranes retaining bacteria from said human fluid sample.

14. An apparatus as claimed in claim 13 wherein said housing is provided with a luer lock means on one section and attachment means on the other section which is adapted to be secured to a lure lock means.

15. An apparatus as claimed in claim 13 wherein said filter membrane positioned upstream from a filter membrane of smaller pore size has a five micron pore size to trap polymorphnuclear leukocytes.

16. An apparatus as claimed in claim 15 wherein said filter membrane also traps lymphocytes.

17. An apparatus as claimed in claim 15 wherein said filter membrane is constructed of polycarbonate.

18. An apparatus as claimed in claim 15 wherein said filter membrane is constructed of nylon.

19. An apparatus as claimed in claim 13 wherein said filter membrane positioned downstream from a filter membrane of larger pore size has a 0.45 micron pore size to trap bacteria.

20. An apparatus as claimed in claim 19 wherein said filter membrane is constructed of nitrocellulose.

21. An apparatus as claimed in claim 13 wherein said human fluid sample is preserved.

22. An apparatus as claimed in claim 13 wherein said human fluid sample is unpreserved.

23. An apparatus for testing for cellular specimens and bacteria in a biological fluid comprising a pump means, a plurality of specimen collection units serially mounted to said pump means for selective removal from each other and said pump means, each said specimen collection unit comprising a separable sectional housing with an inlet and outlet means, said inlet and outlet means additionally serving as connection means with other specimen collection units, a filter membrane means mounted in said housing in one of said housing sections allowing fluid flow therethrough by said biological fluid while selectively retaining either cellular specimens or bacteria dependent upon the pore size of the membrane filter, each filter membrane means in each specimen collection unit has a larger porosity than the filter membrane means in the next downstream specimen collection container.

24. An apparatus for testing as claimed in claim 23 wherein one section of said sectional housing comprises a base, a cylindrical wall extending outward from said base, an interior wall means extending outward from said base positioned inside said cylindrical wall, said interior wall means defining a membrane filter seat and a chamber adjacent said filter seat, a nipple means with a throughgoing bore extends outward from said base in the opposite direction from said cylindrical wall and said interior wall means with the throughgoing bore of the nipple means communicating with said interior wall means chamber.

25. A method of testing for collecting different biological specimens from biological fluid comprising the steps of:
 a. collecting a biological fluid into a container;
 b. passing the biological fluid through a series of separate removably connected sectioned filter containers causing different preselected biological components in the biological fluid to be deposited on membrane filter means held in each sectioned filter container with one of said sectioned filter containers trapping cellular components from the biological fluid;
 c. removing one of the containers which traps the cellular components from the series of separate connected removable sectioned filter containers and opening the filtered sectioned container to provide access to the membrane filter means with trapped cellular components contained therein; and
 d. applying the filter membrane surface to a slide depositing cells on said slide.

26. A method as claimed in claim 25 including the additional step after step c. of preserving the cellular components.

27. A method as claimed in claim 25 including the additional step e. of microscopically examining the deposited cells on said slide.

28. A method of testing for collecting different biological specimens from human body fluid comprising the steps of:
 a. collecting a human body fluid into a container;
 b. passing the human body fluid through a series of separate removably connected sectioned filter containers causing different preselected biological components in the human body fluid to be deposited on membrane filter means held in each sectioned filter container with one of said sectioned filter containers trapping cellular components from the human body fluid;
 c. removing one of the containers which traps the cellular components from the series of separate connected removable sectioned filter containers and opening the filtered sectioned container to provide access to the membrane filter means with trapped cellular components contained therein; and
 d. applying the filter membrane surface to a slide depositing fresh unpreserved cells on said slide.

29. A method as claimed in claim 28 including the additional step e. of microscopically examining the deposited cells on said slide within two hours after the addition of the fresh unpreserved cells to said slide.

30. A method of testing for predetermined biological specimens in a biological fluid comprising the steps of:
 a. collecting a biological fluid into a container;
 b. passing the biological fluid through a series of separate removably connected sectioned filter containers causing different preselected biological components in the biological fluid to be deposited on membrane filter means held in each sectioned filter container with one of said sectioned filter containers trapping bacteria from the biological fluid;
 c. removing the container which traps bacteria from the series of separate connected removable sectioned filter containers and opening the filtered sectioned container to provide access to the membrane filter means with trapped bacteria contained therein;
 d. eluting the trapped bacteria from the membrane filter means into a microbiological culture plate; and
 e. incubating the bacteria into an identifiable bacterial colony.

31. A method of testing for predetermined biological specimens in a biological fluid comprising the steps of:
 a collecting a biological fluid into a container;
 b. passing the biological fluid through a series of separate removably connected sectioned filter containers causing different preselected biological components in the biological fluid to be deposited on membrane filter means held in each sectioned filter container with one of said sectioned filter containers trapping bacteria from the biological fluid;
 c. removing the container which traps bacteria from the series of separate connected removable sectioned filter containers and opening the filtered sectioned container to provide access to the membrane filter means with trapped bacteria contained therein;
 d. eluting the trapped bacteria into a Qualture capsule; and
 e. incubating the bacterial in the Qualture capsule into an identifiable bacterial colony.

32. A method as claimed in claim 31 including the additional step f. of microscopically examining the bacterial colony.

33. A method of testing for predetermined biological specimens in a preserved biological fluid comprising the steps of:
 a. collecting a preserved biological fluid into a container;
 b. passing the preserved biological fluid through a series of separate removably connected sectioned filter containers causing different preselected biological components in the preserved biological fluid to be deposited on membrane filter means held in each sectioned filter container with one of said sectioned filter containers trapping bacteria from the preserved biological fluid;
 c. removing the container which traps bacteria from the series of separate connected removable sectioned filter containers and opening the filtered sectioned container to provide access to the membrane filter means with trapped bacteria contained therein;
 d. eluting the trapped bacteria from the membrane filter means onto a slide; and
 e. microscopically examining the deposited bacteria on said slide.

* * * * *